United States Patent
Lee et al.

(10) Patent No.: US 11,684,339 B2
(45) Date of Patent: Jun. 27, 2023

(54) APPARATUS AND METHOD FOR ESTIMATING BIO-INFORMATION, ULTRASONIC DEVICE, AND MOBILE DEVICE

(71) Applicant: SAMSUNG ELECTRONICS CO., LTD., Suwon-si (KR)

(72) Inventors: So Young Lee, Daejeon (KR); Jong Keun Song, Yongin-si (KR); Byung Hoon Ko, Hwaseong-si (KR); Hyun Seok Moon, Hwaseong-si (KR); Sang Kon Bae, Seongnam-si (KR); Eui Seok Shin, Yongin-si (KR); Jeong Eun Hwang, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 322 days.

(21) Appl. No.: 16/992,799

(22) Filed: Aug. 13, 2020

(65) Prior Publication Data

US 2021/0251508 A1  Aug. 19, 2021

(30) Foreign Application Priority Data

Feb. 17, 2020 (KR) .................. 10-2020-0019097

(51) Int. Cl.
- *A61B 8/08* (2006.01)
- *A61B 5/145* (2006.01)
- *A61B 8/00* (2006.01)

(52) U.S. Cl.
CPC .......... *A61B 8/0891* (2013.01); *A61B 8/4227* (2013.01); *A61B 8/463* (2013.01); *A61B 8/5223* (2013.01); *A61B 8/54* (2013.01)

(58) Field of Classification Search
None
See application file for complete search history.

(56) References Cited

U.S. PATENT DOCUMENTS

| 8,235,897 B2 | 8/2012 | Gal et al. |
| 9,713,447 B2 | 7/2017 | Caduff et al. |
| (Continued) | | |

FOREIGN PATENT DOCUMENTS

| JP | 4799833 B2 | 10/2011 |
| JP | 2016-43093 A | 4/2016 |
| (Continued) | | |

OTHER PUBLICATIONS

Kawano et al. Hyperglycemia Rapidly Suppresses Flow-Mediated Endothelium-Dependent Vasodilation of Brachial Artery. J Am Coll Cardiol. Jul. 1999;34(1): 146-54. (Year: 1999).*

(Continued)

*Primary Examiner* — Meredith Weare
(74) *Attorney, Agent, or Firm* — Sughrue Mion, PLLC

(57) ABSTRACT

An apparatus for estimating bio-information is provided. The apparatus includes: an ultrasound image acquirer configured to acquire ultrasound images of an object; a pressurizer configured to apply pressure to the object to occlude a blood vessel; and a processor configured to estimate a change in a diameter of the blood vessel using the ultrasound images acquired by the ultrasound image acquirer before and after an occlusion of the blood vessel, and estimate bio-information based on the estimated change in the diameter of the blood vessel.

28 Claims, 11 Drawing Sheets

(56) References Cited

U.S. PATENT DOCUMENTS

| | | | |
|---|---|---|---|
| 2002/0198443 A1 | 12/2002 | Ting | |
| 2008/0119743 A1* | 5/2008 | Friedman | A61B 8/4227 |
| | | | 600/490 |
| 2014/0288446 A1* | 9/2014 | Lee | A61B 5/022 |
| | | | 600/493 |
| 2016/0029972 A1 | 2/2016 | Lenehan et al. | |
| 2016/0058305 A1* | 3/2016 | Nichol | A61B 5/7282 |
| | | | 600/504 |
| 2016/0174853 A1 | 6/2016 | Cho et al. | |
| 2017/0258386 A1 | 9/2017 | Woltjer et al. | |
| 2018/0035930 A1 | 2/2018 | Sokolov et al. | |
| 2018/0055454 A1 | 3/2018 | Newberry | |
| 2018/0092631 A1 | 4/2018 | Liou | |
| 2019/0216338 A1* | 7/2019 | Lee | A61B 5/7275 |
| 2019/0269381 A1 | 9/2019 | Masuda et al. | |
| 2020/0315571 A1* | 10/2020 | Sonnenschein | A61B 8/06 |

FOREIGN PATENT DOCUMENTS

| | | |
|---|---|---|
| KR | 1020100008073 A | 1/2010 |
| KR | 1020100022614 A | 3/2010 |
| KR | 1020160075230 A | 6/2016 |

OTHER PUBLICATIONS

Gori et al. "Conduit Artery Constriction Mediated by Low Flow." J Am Coll Cardiol. May 20, 20080;51(20):1953-8. (Year: 2008).*

Communication dated Jul. 9, 2021 issued by the European Patent Office in European Application No. 20196188.5.

Alessandro Ramalli et al., "Continuous Simultaneous Recording of Brachial Artery Distension and Wall Shear Rate: A New Boost for Flow-Mediated Vasodilation", IEEE Transactions on Ultrasonics, Ferroelectrics and Frequency Control, Mar. 1, 2019, vol. 66, No. 3, pp. 463-471 (9 pages total).

Communication dated Apr. 26, 2021, from the European Patent Office in European Application No. 20196188.5.

Heitmar, R., et al., "Retinal vessel diameters and reactivity in diabetes mellitus and/or cardiovascular disease", Cardiovascular Diabetology, 2017, vol. 16, No. 56, pp. 1-10 (11 pages).

Blair, N., et al., "Retinal Oximetry and Vessel Diameter Measurements With a Commercially Available Scanning Laser Ophthalmoscope in Diabetic Retinopathy", IOVS, Oct. 2017, vol. 58, No. 12, pp. 5556-5563.

Lee, J-W., et al., "Comparison of Endothelium-Dependent Vasodilation According to the Presence of Diabetes in Coronary Artery Disease", Korean Circulation Journal, 2005, vol. 35, pp. 910-915.

V., Z., et al., "Simulation Studies for Noninvasive Optical Measurements of Blood-Scattering Changes in a Skin Model with a Large Blood Vessel", Current Optics and Photonics, vol. 3, No. 1, Feb. 2019, pp. 46-53.

Kurasawa, S., et al., "Verification of Non-Invasive Blood Glucose Measurement Method Based on Pulse Wave Signal Detected by FBG Sensor System", Sensors, 2017, vol. 17, No. 2702, pp. 1-13.

* cited by examiner

APPARATUS AND METHOD FOR ESTIMATING BIO-INFORMATION, ULTRASONIC DEVICE, AND MOBILE DEVICE

CROSS-REFERENCE TO RELATED APPLICATION(S)

This application claims priority under 35 U.S.C. § 119(a) to Korean Patent Application No. 10-2020-0019097, filed on Feb. 17, 2020, in the Korean Intellectual Property Office, the entire disclosure of which is herein incorporated by reference for all purposes.

BACKGROUND

1. Field

Example embodiments relate to estimating bio-information, and more particularly, to estimating bio-information based on a change in a diameter of a blood vessel based on ultrasonic waves.

2. Description of Related Art

Patients with hypertension, hyperlipidemia, diabetes, heart disease, or obesity may have atherosclerosis when endothelial cell-dependent vasodilation is impaired due to a decreased vascular endothelial function. In general, there are invasive and non-invasive methods of diagnosing a vascular endothelial dysfunction. An invasive diagnostic method may acquire a relatively accurate test result, but the test procedures are complicated and is generally difficult to use as a screening method for endothelial examination. A flow mediated dilation (FMD) test method is one of typical non-invasive diagnostic methods. An FMD test requires proficient measurement skills of an examiner or the like, such as measuring an inner diameter and a blood flow velocity of a blood vessel by continually finding the blood vessel at the same location during the test, and has a limitation in that test results between examiners may be inconsistent.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an example embodiment, there is provided an apparatus for estimating bio-information, the apparatus including: an ultrasound image acquirer configured to acquire ultrasound images of an object; a pressurizer configured to apply pressure to the object to occlude a blood vessel; and a processor configured to estimate a change in a diameter of the blood vessel using the ultrasound images acquired by the ultrasound image acquirer before and after an occlusion of the blood vessel, and configured to estimate bio-information based on the estimated change in the diameter of the blood vessel.

The ultrasound image acquirer may be further configured to transmit ultrasonic waves to the object, receive a reflected wave reflected from the object, and generate the ultrasound images based on the received reflected wave.

The pressurizer may include a cuff.

The processor may be further configured to, based on a request for estimating the bio-information, control the ultrasound image acquirer to acquire the ultrasound images, and control the pressurizer to apply the pressure to the object during a period of time, and release the pressure after an elapse of the period of time.

The processor may be further configured to, based on the estimated change in the diameter of the blood vessel, acquire at least one feature among a vascular contraction rate, a vascular dilation rate, a restoration rate, and a vascular diameter change trend of the blood vessel, and estimate the bio-information based on the acquired at least one feature.

The processor may be further configured to generate a graph representing the estimated change in the diameter of the blood vessel over a period of time and acquire the at least one feature based on the generated graph.

The processor may be further configured to acquire the vascular contraction rate based on a difference between a diameter of the blood vessel before pressurization and a reduced blood vessel diameter after the pressurization.

The processor may be further configured to acquire the vascular dilation rate based on a difference between a diameter of the blood vessel before pressurization and a diameter of a dilated blood vessel.

The processor may be further configured to acquire the restoration rate of the blood vessel based on a slope between a diameter of a dilated blood vessel at a first time point at which the dilated blood vessel occurs upon releasing the pressure and a diameter of the blood vessel after a predetermined time from the first time point.

The processor may be further configured to, based on the acquired at least one feature, estimate the bio-information using a bio-information estimation model, the bio-information estimation model defining a correlation between the at least one feature and the bio-information.

The bio-information may include information of at least one of blood sugar, glucose intake, calories, triglycerides, proteins, cholesterol, carotenoids, lactic acid, body water, extracorporeal water, total body water, and uric acid.

The apparatus may further include an output interface configured to output at least one of the ultrasound images, the change in the diameter of the blood vessel, and a result of estimating the bio-information.

According to an aspect of an example embodiment, there is provided a method of estimating bio-information, including: acquiring, through an ultrasound image acquirer, ultrasound images of an object; pressurizing, through a pressurizer, the object to occlude a blood vessel; estimating, by a processor, a change in a diameter of the blood vessel using the ultrasound images acquired by the ultrasound image acquirer before and after an occlusion of the blood vessel; and estimating, by the processor, bio-information based on the estimated change in the diameter of the blood vessel.

The estimating the bio-information may include acquiring, based on the change in the diameter of the blood vessel, at least one feature among a vascular contraction rate, a vascular dilation rate, a restoration rate, and a vascular diameter change trend of the blood vessel, and estimating the bio-information based on the acquired at least one feature.

The acquiring the at least one feature may include acquiring the vascular contraction rate based on a difference between a diameter of the blood vessel before pressurization and a reduced blood vessel diameter after the pressurization.

The acquiring the at least one feature may include acquiring the vascular dilation rate based on a difference between a diameter of the blood vessel before pressurization and a diameter of a dilated blood vessel.

The acquiring the at least one feature may include acquiring the restoration rate of the blood vessel based on a slope between a diameter of a dilated blood vessel at a first time point at which the dilated blood vessel occurs upon releasing pressure and a diameter of the blood vessel after a predetermined time from the first time point.

The estimating the bio-information based on the acquired at least one feature may include estimating the bio-information using a bio-information estimation model, the bio-information estimating defining a correlation between the at least one feature and the bio-information.

The method may further include outputting at least one of the change in the diameter of the blood vessel, and a result of estimating the bio-information.

According to an aspect of an example embodiment, there is provided an ultrasonic device including: an ultrasound image acquirer configured to transmit ultrasonic waves to an object and acquire ultrasound images based on a reflected wave reflected from the object; and a processor configured to control a pressurizing device to occlude a blood vessel of the object, estimate a change in a diameter of the blood vessel based on the ultrasound images acquired by the ultrasound image acquirer before and after an occlusion of the blood vessel, and estimate bio-information based on the estimated change in the diameter of the blood vessel.

The ultrasonic device may further include a communication interface configured to transmit a control signal generated by the processor to the pressurizing device.

The communication interface may be further configured to transmit at least one of the ultrasound images, the change in the diameter of the blood vessel, and a result of estimating the bio-information to a mobile device.

The processor may be further configured to acquire, based on the change in the diameter of the blood vessel, at least one feature among a vascular contraction rate, a vascular dilation rate, a restoration rate, and a vascular diameter change trend of the blood vessel, and estimate the bio-information using the acquired at least one feature.

The ultrasonic device may further include an output interface configured to output at least one of the ultrasound images, the change in the diameter of the blood vessel, and a result of estimating the bio-information.

The ultrasonic device may further include a main body in which the ultrasound image acquirer and the processor are mounted; and a strap configured to be connected to the main body.

According to an aspect of an example embodiment, there is provided a mobile device including: a communication interface configured to transmit a first control signal to an ultrasonic device and a second control signal to a pressurizing device and receive ultrasound images of an object from the ultrasonic device; and a processor configured to: generate the first control signal and the second control signal; estimate a change in a diameter of a blood vessel based on the ultrasound images transmitted from the ultrasonic device before and after an occlusion of the blood vessel; and estimate bio-information based on the estimated change in the diameter of the blood vessel.

The processor may be further configured to: generate, based on a request for estimating the bio-information, the first control signal for controlling the ultrasonic device to acquire the ultrasound images; generate the second control signal for controlling the pressurizing device to pressurize the object during a period of time; and generate a third control signal for controlling the pressurizing device to release pressure after an elapse of the period of time.

The processor may be further configured to, based on the estimated change in the diameter of the blood vessel, acquire at least one feature among a vascular contraction rate, a vascular dilation rate, a restoration rate, and a vascular diameter change trend of the blood vessel, and estimate the bio-information based on the acquired at least one feature.

The mobile device may further include an output interface configured to output at least one of the ultrasound images, the change in the diameter of the blood vessel, and a result of estimating the bio-information.

BRIEF DESCRIPTION OF THE DRAWINGS

The above and other aspects, features, and advantages of certain example embodiments of the disclosure will be more apparent from the following description taken in conjunction with the accompanying drawings, in which.

DETAILED DESCRIPTION

Figure 1:
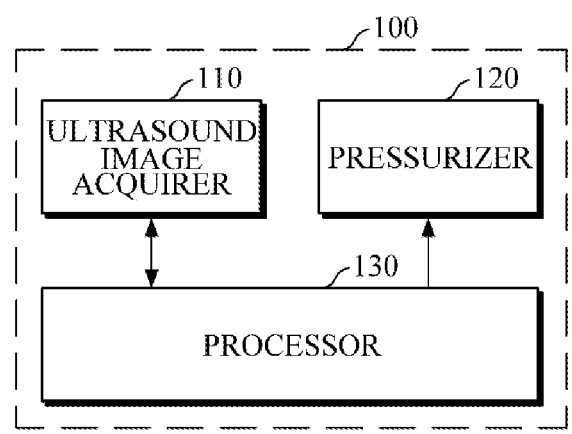
FIG. 1 is a block diagram illustrating an apparatus for estimating bio-information according to an example embodiment.

Details of example embodiments are provided in the following detailed description with reference to the accompanying drawings. The disclosure may be understood more readily by reference to the following detailed description of example embodiments and the accompanying drawings. Throughout the drawings and the detailed description, unless otherwise described, the same drawing reference numerals will be understood to refer to the same elements, features, and structures. The relative size and depiction of these elements may be exaggerated for clarity, illustration, and convenience.

The disclosure may, however, be embodied in many different forms and should not be construed as being limited to the embodiments set forth herein. Rather, these embodiments are provided so that the disclosure will be thorough and complete and will fully convey the concept of the invention to those skilled in the art, and the disclosure will only be defined by the appended claims.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as "unit" and "module" denote units that process at least one function or operation, and they may be implemented by using hardware, software, or a combination of hardware and software.

As used herein, the term "and/or" includes any and all combinations of one or more of the associated listed items. Expressions such as "at least one of," when preceding a list of elements, modify the entire list of elements and do not modify the individual elements of the list. For example, the expression "at least one of a, b, and c," should be understood as including only a, only b, only c, both a and b, both a and c, both b and c, or all of a, b, and FIG. 1 is a block diagram illustrating an apparatus for estimating bio-information according to an example embodiment.

Referring to FIG. 1, an apparatus 100 for estimating bio-information includes an ultrasound image acquirer 110, a pressurizer 120, and a processor 130. The ultrasound image acquirer 110, the pressurizer 120, and the processor 130 may be integrally provided in one hardware device or separately provided in two or more hardware devices.

The ultrasound image acquirer 110 may transmit ultrasonic waves to an object under the control of the processor 130 and acquire an ultrasound image of the object based on a reflected wave reflected from the object. The ultrasound image acquirer 110 may include an ultrasonic transducer which converts an electrical signal into an ultrasonic signal or converts an ultrasonic signal into an electrical signal. The ultrasonic transducer may include a linear one-dimensional or two-dimensional array of ultrasonic elements to acquire the ultrasound image. The ultrasonic elements may be piezoelectric elements.

For example, an array pitch may be, in the case of a one-dimensional array, 70 channels or more in order to secure an aperture of 2 cm, or may be, in the case of a two-dimensional array, 2100 channels or more in order to secure an aperture of 2 cm in a lateral direction (or a row direction) and an aperture of 1 cm in an elevation direction (or a column direction). However, the example embodiments are not limited thereto, and the ultrasonic transducer may include various configurations, such as a 1.5-dimensional or 1.75-dimensional array. A center frequency of the ultrasonic transducer may be greater than or equal to 5 MHz, and smaller than or equal to 15 MHz, and a power consumption of the ultrasonic transducer may be 2 W or less during driving.

The pressurizer 120 may perform a function of applying pressure to the object to block the blood vessel in the object or releasing occlusion. For example, the pressurizer 120 may include a cuff.

The processor 130 may control the ultrasound image acquirer 110 and the pressurizer 120 using wired or wireless communication and estimate bio-information based on the ultrasound image of the object obtained by the ultrasound image acquirer 110. In this case, the object may include, for example, a wrist skin region adjacent to a radial artery and a human skin region through which capillary or venous blood passes. However, the object is not limited thereto and may be a peripheral region of the human body, such as a finger or a toe, which is a region where a blood vessel density is high in the human body.

When a request for estimating bio-information is received, the processor 130 may control the ultrasound image acquirer 110 to acquire an ultrasound image for a predetermined time, and after a first predetermined time elapses, the processor 130 may control the pressurizer 120 to gradually pressure the object and occlude the blood vessel. In addition, when a second predetermined time elapses after the blood vessel of the object is occluded according to the pressure, the processor 130 may control the pressurizer 120 to release the pressure.

The processor 130 may estimate a change in a diameter of the blood vessel by analyzing the ultrasound images acquired by the ultrasound image acquirer 110 before and after the occlusion of the blood vessel. In addition, the bio-information may be estimated based on the change in a diameter of the blood vessel. The bio-information may include information on at least one of blood sugar, glucose intake, calories, triglycerides, proteins, cholesterol, carotenoids, lactic acid, body water, extracorporeal water, total body water, and uric acid, but is not limited thereto.

The processor 130 may extract a feature based on the change in a diameter of the blood vessel before and after the occlusion of the blood vessel and estimate the bio-information based on the extracted feature. The extracted feature may include information, such as a vascular contraction rate, a vascular dilation rate, a restoration degree (or a restoration rate) of blood vessels, a vascular diameter change trend, and the like. However, the extracted feature used in estimating the bio-information is not limited thereto.

Figure 3:
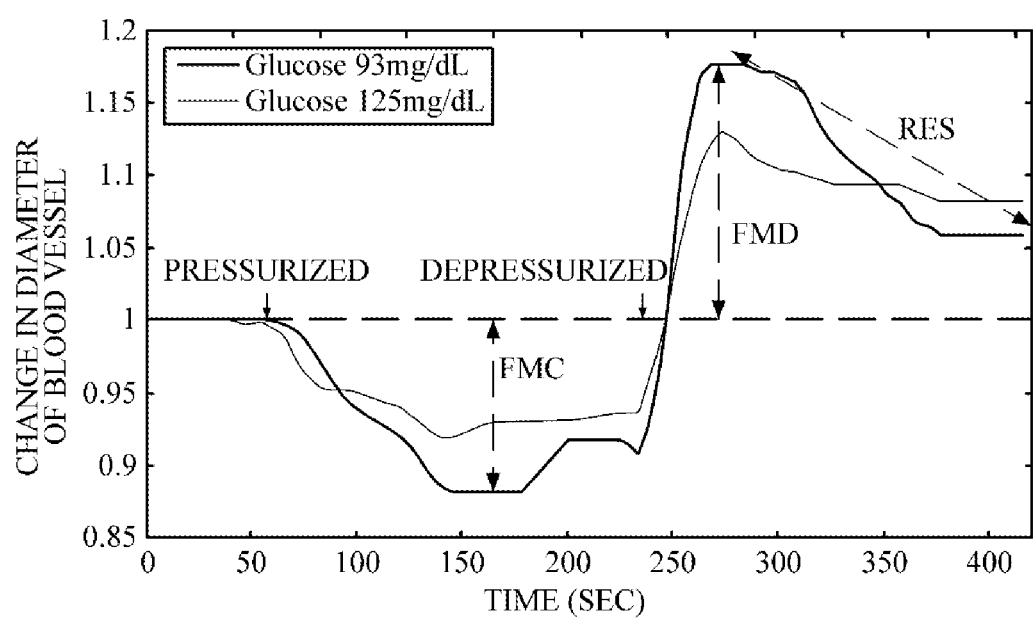
FIG. 3 is a graph of change in a diameter of a blood vessel before and after vessel occlusion.

FIG. 3 is a graph of change in a diameter of a blood vessel before and after occlusion of a blood vessel in a fasting state (e.g., corresponding to a glucose level of 93 mg/dL) and in a state in which a blood sugar level is elevated (e.g., corresponding to a glucose level of 125 mg/dL) after food intake.

The processor 130 may monitor the change in a diameter of the blood vessel over a predetermined period of time. In an example embodiment, the processor 130 may generate a graph showing the change in the diameter of the blood vessel over a predetermined period of time. Referring to FIG. 3, the X-axis of the graph of change in a diameter of the blood vessel represents a time of acquiring an ultrasound image, and the Y-axis represents a change rate of a blood vessel diameter which is normalized to "1" before the pressurizer 120 pressurizes the object. Referring to FIG. 3, it can be seen that, when the blood sugar level increases and hyperglycemia occurs, cells are stressed and produce free oxygen radicals, thereby decreasing activation of vasodilator nitric oxide (NO) and, in turn, reducing a vasodilation response before and after the occlusion of the blood vessel.

Referring to FIG. 3, the processor 130 may acquire a vascular contraction rate (or flow mediated contraction (FMC)) based on a difference between a reduced diameter of the blood vessel occluded by pressurization and a diameter of the blood vessel before pressurization. For example, the vascular contraction rate (FMC) may be obtained by dividing a value, obtained by subtracting the reduced diameter of the blood vessel from the blood vessel diameter before pressurization, by the blood vessel diameter before pressurization. In this case, the reduced diameter of the blood vessel may be a minimum diameter value obtained in a state in which the blood vessel diameter is minimized according to the pressurization or may be an average diameter value obtained in a specific section after the pressurization. However, the reduced diameter of the blood vessel is not limited thereto.

In addition, the processor 130 may acquire a vascular dilation rate (or flow mediated dilatation (FMD)) based on a difference between the vessel diameter before the pressurization and the diameter of the dilated blood vessel which is restored upon releasing the pressure. For example, the vascular dilation rate (FMD) may be acquired by dividing a value, obtained by subtracting the blood vessel diameter before the pressurization from the diameter of the dilated blood vessel, by the blood vessel diameter before the pressurization. In this case, the diameter of the dilated blood vessel may be a maximum diameter value obtained in a state in which the blood vessel diameter is maximized as the pressure is released or an average diameter value obtained in a specific section after releasing the pressure. However, the diameter of the dilated blood vessel is not limited thereto.

In addition, the processor 130 may acquire a restoration degree (RES) of the blood vessel indicating a degree (or a rate) at which the blood vessel is restored, based on a slope between the diameter of the dilated blood vessel at a time point at which the dilated blood vessel occurs upon releasing the pressure and the diameter of the blood vessel after a predetermined time from the time point at which the dilated blood vessel occurs upon releasing the pressure. For example, the acquired slope value or a value obtained by applying a predefined function to the acquired slope value may be determined as the restoration degree (RES) of the blood vessel.

In addition, the processor 130 may analyze a trend of a change in a diameter of the blood vessel, for example, a vascular dilation rate, a vascular contraction rate, and the slope of the restoration degree of the blood vessel, based on a history of information on bio-information estimation (hereinafter, referred to as bio-information estimation history information) for a predetermined period of time.

The processor 130 may combine one or more features extracted based on the change in a diameter of the blood vessel before and after the occlusion of the blood vessel and estimate the bio-information using a bio-information estimation model that defines a correlation between the one or more features and the bio-information. The bio-information estimation model may be in a form of a linear function, but is not limited thereto, and may be defined through various methods, such as linear/nonlinear regression analysis, neural network, deep learning, and the like.

For example, the biometric information estimation model based on a vascular dilation rate may be represented by the following Equation 1.

$$Y = FMD1 + bFMD2 \quad \text{[Equation 1]}$$

Here, FMD1 denotes a vascular dilation rate in a fasting state and FMD2 denotes a vascular dilation rate when blood sugar is elevated. b denotes a calibration coefficient and may be a value defined for each individual. Y denotes the amount of a change in blood sugar.

When the amount of the change in blood sugar is acquired, the processor 130 may acquire a blood sugar estimation value by adding a fasting blood sugar level (or a blood sugar level in a fasting state) to the amount of the change in blood sugar.

Figure 2:
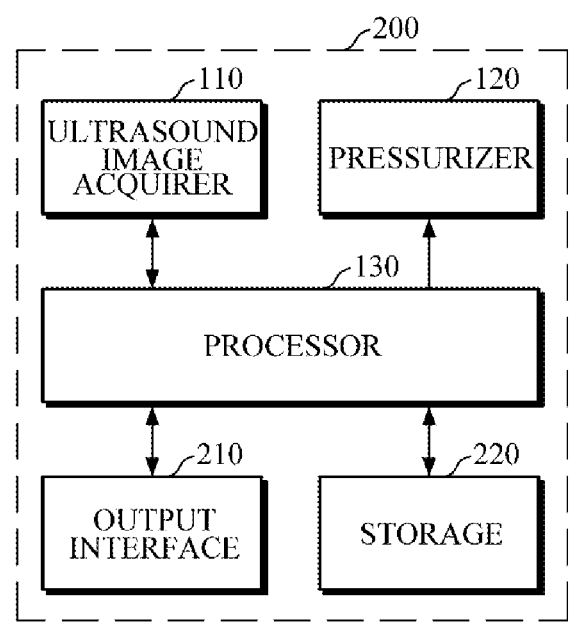
FIG. 2 is a block diagram illustrating an apparatus for estimating bio-information according to another example embodiment.

FIG. 2 is a block diagram illustrating an apparatus for estimating bio-information according to another example embodiment.

Referring to FIG. 2, another example embodiment of an apparatus 200 for estimating bio-information may include an ultrasound image acquirer 110, a pressurizer 120, a processor 130, an output interface 210, and a storage 220. The ultrasound image acquirer 110, the pressurizer 120, and the processor 130 have been described in detail above, and thus detailed descriptions thereof will be omitted.

The output interface 210 may provide an ultrasound image acquired by the ultrasound image acquirer 110 and a processing result of the processor 200 to a user. For example, the output interface 210 may visually output the ultrasound image and the processing result through a visual output module, such as a display.

For example, the output interface 210 may divide the display into two or more areas, and display, in a first area, basic information used in estimating bio-information, for example, a graph of a change in a blood vessel diameter, a vascular dilation rate, a vascular contraction rate, a restoration rate of a blood vessel, and the like, which are used for estimating bio-information. In addition, information, such as a bio-information estimated value, warning information indicating an abnormal value of the estimated bio-information, corrective measures, and the like, may be displayed in a second area. In this case, when the bio-information estimated value is out of a normal range, the bio-information may be highlighted by a certain color (e.g., red color) or the normal range may be displayed together.

In another example, the output interface 210 may provide the bio-information estimation result to the user in a non-visual manner, such as voice, vibration, and tactile sensation, by using a voice output module, such as a speaker, or a haptic module, such as a vibrator, alone or together with a visual display.

The storage 220 may store information such as reference information, the change in a diameter of a blood vessel, extracted features, and the like that is used for bio-information estimation. The reference information may include user characteristic information, such as age, gender, health status, and the like of the user, and information of a bio-information estimation model.

The storage 220 may include at least one type of a storage medium such as, for example, a flash memory type, a hard disk type, a multimedia card micro type, a card type memory (for example, secure digital (SD) or extreme digital (XD) memory), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk, but is not limited thereto.

Figure 4:
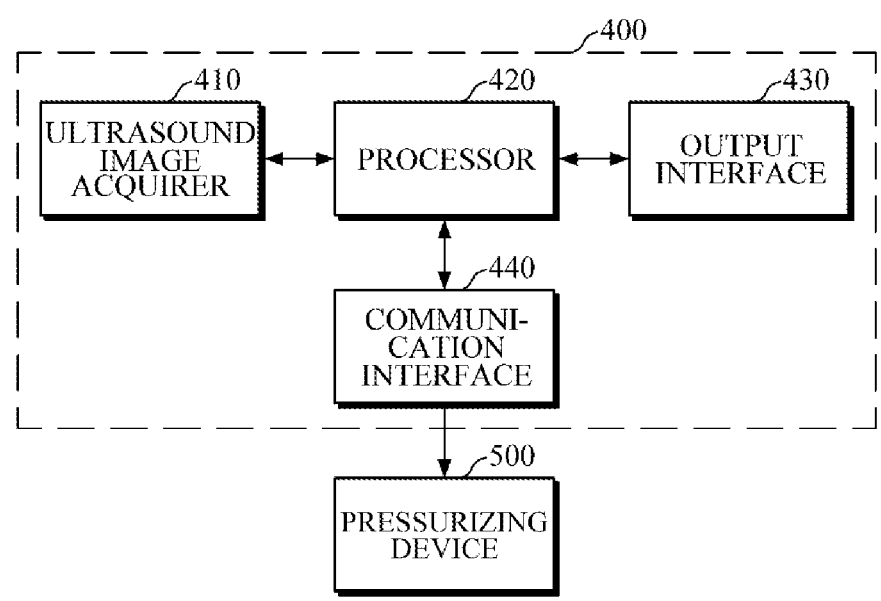
FIG. 4 is a block diagram illustrating an ultrasonic device according to an example embodiment.
Figure 5A:
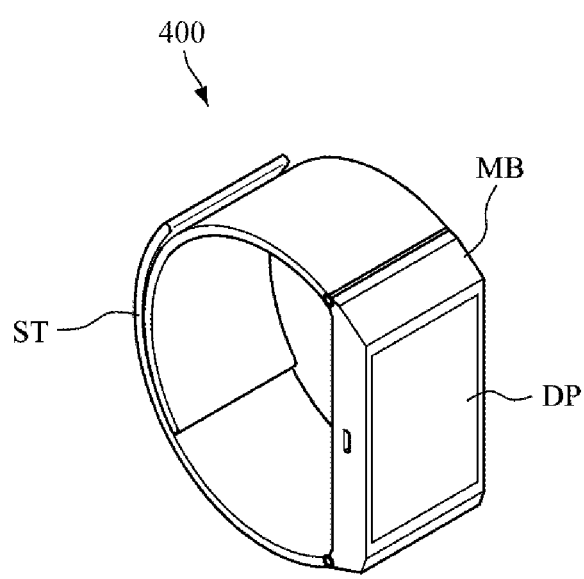
FIGS. 5A, 5B, and 5C illustrate an ultrasonic device in a form of a wearable device according to example embodiments.
Figure 5B:
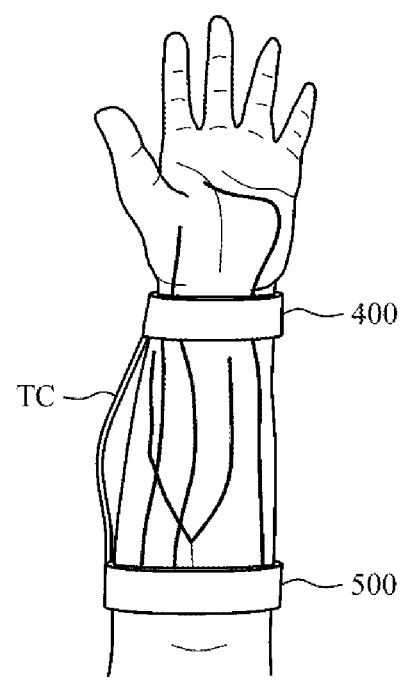
Figure 5C:
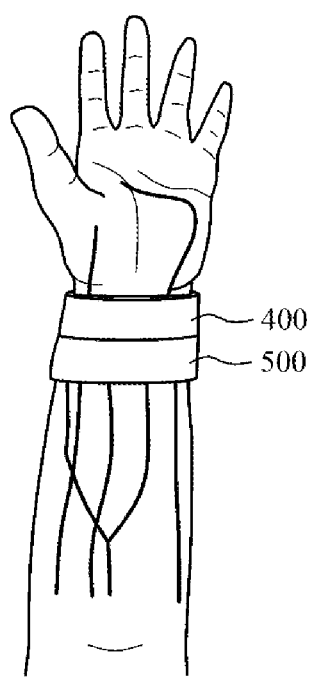

FIG. 4 is a block diagram illustrating an ultrasonic device according to an example embodiment. FIGS. 5A, 5B, and 5C illustrate an ultrasonic device in a form of a wearable device according to example embodiments.

Referring to FIG. 4, an ultrasonic device 400 according to an example embodiment may include an ultrasound image acquirer 410, a processor 420, an output interface 430, and a communication interface 440.

The ultrasound image acquirer 410 may transmit ultrasonic waves to an object under the control of the processor 420 and acquire an ultrasound image of the object based on a reflected wave reflected from the object. The ultrasound image acquirer 410 has been described in detail above, and thus a detailed description thereof will not be reiterated.

The processor 420 may be electrically connected to the ultrasound image acquirer 410. When a request for estimating bio-information is received, the processor 420 may control the ultrasound image acquirer 410 to acquire the ultrasound image.

In addition, the processor 420 may control a pressurizing device 500 to pressurize the object while the ultrasound image is acquired, and control the pressurizing device 500 to release the pressure after a predetermined period of time. In an example embodiment, the pressurizing device 500 may be a separate external hardware device.

The processor 420 may be connected to the pressurizing device 500 through wireless communication, generate a control signal for controlling the pressurizing device 500, and transmit the generated control signal to the pressurizing device 500 through the communication interface 440.

The processor may estimate the change in a diameter of a blood vessel based on ultrasound images acquired before and after occlusion of a blood vessel according to pressurizing and releasing of pressure. In this case, the processor 420 may execute an algorithm that calculates a diameter of a blood vessel by analyzing the ultrasound images. Also, the processor 420 may execute a bio-information estimation algorithm to extract features, such as a vascular dilation rate, a vascular contraction rate, a restoration rate of a blood vessel, and the like, and may estimate bio-information based on the features by using a bio-information estimation model.

The output interface 430 may output at least one of the ultrasound images acquired by the ultrasound image acquirer 410, the blood vessel diameter change, and the bio-information estimation result. In an example embodiment, the output interface 430 may include, for example, a visual output module such as a display, a voice output module such as a speaker, or a haptic module such as a vibrator.

The communication interface 440 may communicate with the pressurizing device 500 and an external device such as a mobile device using a communication technology. The communication interface 440 may acquire a control signal for ultrasound image acquisition and/or a control signal for controlling the pressurizing device 500 from the mobile device and transmit the received control signal to the processor 420. The communication interface 440 may transmit the ultrasound images acquired by the ultrasound image acquirer 410, the blood vessel diameter change estimated by the processor 420, the extracted features, and the bio-information estimation result, and the like to the mobile device.

The communication technology may include Bluetooth communication, Bluetooth low energy (BLE) communication, near field communication, wireless local access network (WLAN) communication, Zigbee communication, infrared data association (IrDA) communication, wireless fidelity (Wi-Fi) direct (WFD) communication, ultra wideband (UWB) communication, Ant+ communication, Wi-Fi communication, and third generation (3G), fourth generation (4G), and fifth generation (5G) communication technologies. However, the communication technology is not limited to the above examples.

FIG. 5A illustrates an example embodiment of the ultrasonic device 400 provided as a smart watch or as a smart band-type wearable device. However, the example embodiment is not limited thereto and the ultrasonic device 400 may be provided in a form of an accessory, such as a bracelet.

As illustrated, the ultrasonic device 400 in a form of a smart watch may include a main body MB and a strap ST.

The main body MB may be provided in various shapes. The main body MB may be equipped with an ultrasound image acquirer 410, a processor 420, an output interface 430, a communication interface 440, and components that perform other functions related to bio-information estimation. A battery for supplying power to various components of the ultrasonic device 400 may be built in the main body MB or the strap ST.

The strap ST may be connected to the main body MB. The strap ST may be flexible so as to be bent to wrap around a user's wrist. As illustrated, the strap ST may include separate members capable of being coupled to each other or may be in an integrated form (e.g., an integrated band).

A display DP may be disposed above the main body MB. The output interface 430 may display a bio-information estimation result estimated by the processor 420 on the display DP. The display DP may include a touch panel capable of receiving a touch input. When the touch input of the user is received through the display DP, the output interface 430 may transmit the received touch input to the processor 420.

In addition, the main body MB may be equipped with a storage that stores the processing result of the processor 420 and variety of information.

In addition, an operator that receives a user's control command and transmits the same to the processor 420 may be mounted on a side of the main body MB. The operator may include a power button for receiving a command to turn on/off the ultrasonic device 400.

Referring to FIGS. 5B and 5C, the ultrasonic device 400 may be worn on a wrist portion of an object, and the pressurizing device 500 may be provided as a separate hardware device and may be worn at a position spaced apart from the ultrasonic device 400. The ultrasonic device 400 and the pressurizing device 500 may be electrically connected to each other through a cable TC. As illustrated in FIG. 5C, the ultrasonic device 400 and the pressurizing device 500 may be provided as one set to appear as a single unit when disposed in a close proximity or contact with each other.

When the ultrasonic device 400 acquires the ultrasound image from a blood vessel region of the user's wrist, the pressurizing device 500 may control the processor 420 of the ultrasonic device 400 through the electric cable TC to pressurize the user's arm and occlude the blood vessel. Alternatively, the pressurizing device 500 may include a communication module therein, and may receive a control signal from the ultrasonic device 400 or a mobile device through wireless communication.

The pressurizing device 500 may be provided in the strap ST of the ultrasonic device 400. For example, the strap ST may be filled with air or have an airbag to have elasticity according to a change in pressure applied to the wrist.

Figure 6:
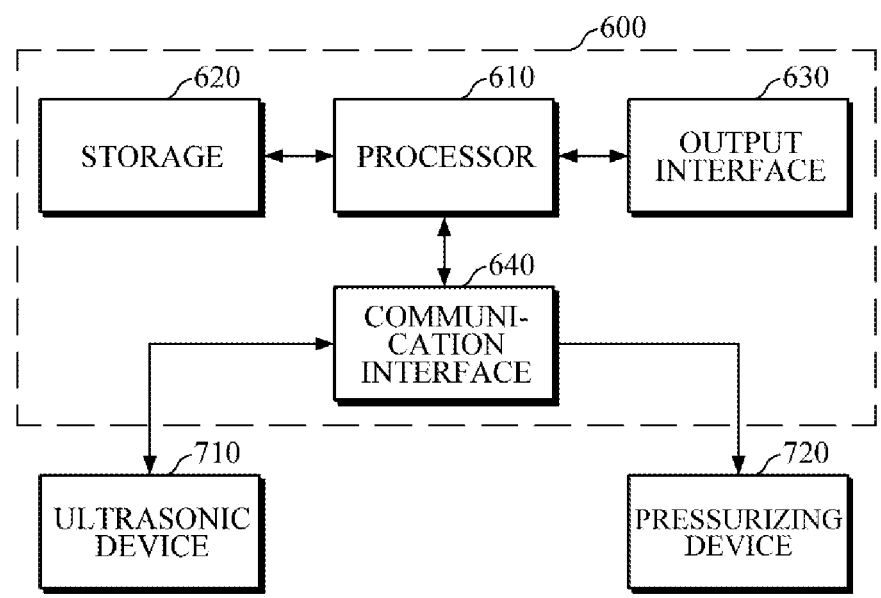
FIG. 6 is a block diagram illustrating a mobile device according to an example embodiment.
Figure 7A:
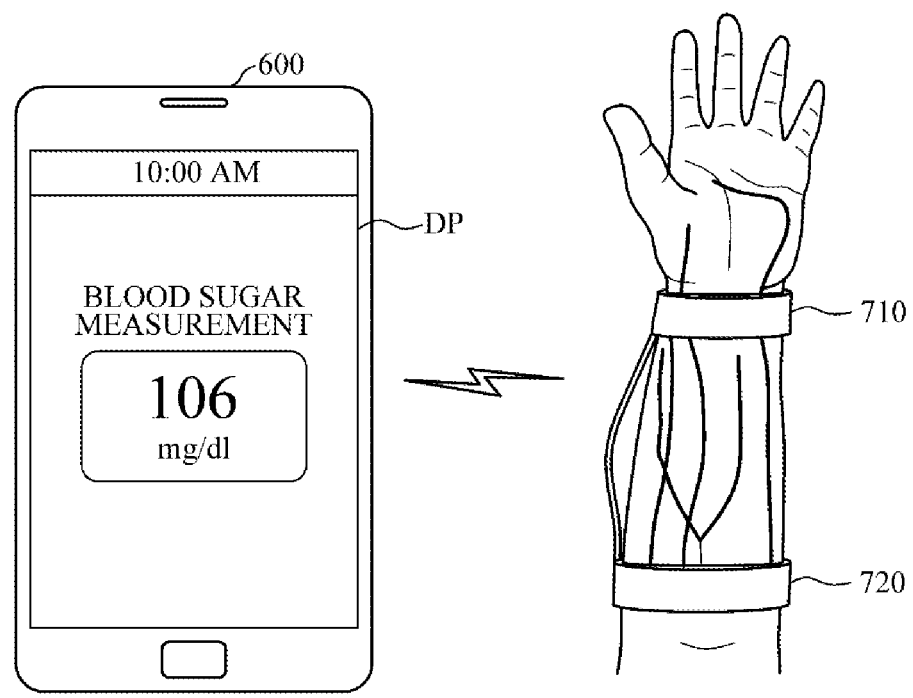
FIGS. 7A and 7B are diagrams for describing a function of estimating blood sugar in a mobile device according to an example embodiment.
Figure 7B:
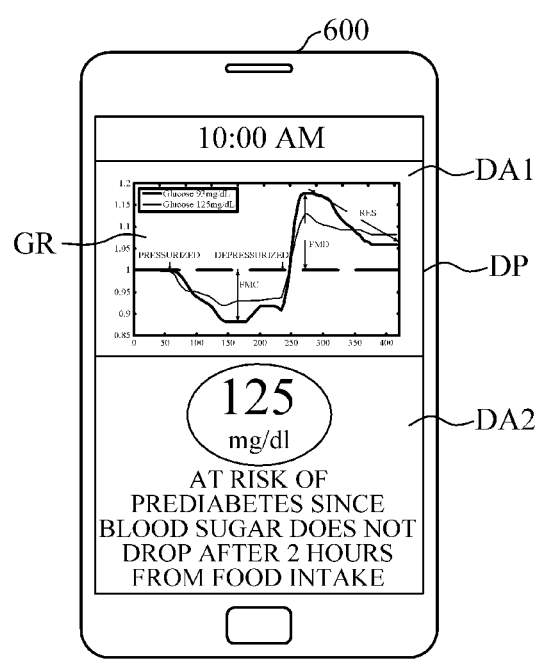

FIG. 6 is a block diagram illustrating a mobile device according to an example embodiment. FIGS. 7A and 7B are diagrams for describing a blood sugar estimating function of a mobile device according to an example embodiment.

Referring to FIG. 6, the mobile device 600 may include a processor 610, a storage 620, an output interface 630, and a communication interface 640.

When the processor 610 receives a request for estimating bio-information, the processor 610 may generate a control signal for controlling an external ultrasonic device 710 and a pressurizing device 720 with reference to the information stored in the storage 620, and transmit the control signal to the ultrasonic device 710 and the pressurizing device 720 through the communication interface 640. The control signal for controlling the pressurizing device 720 may be transmitted to the ultrasonic device 710 rather than being directly transmitted to the pressurizing device 720, and the ultrasonic device 710 may transmit the received control signal to the electrically connected pressurizing device 720.

In addition, when the processor 610 receives ultrasound images before and after occlusion of a blood vessel from the ultrasonic device 710, the processor 610 may estimate the change in a diameter of the blood vessel by executing a blood vessel diameter calculation algorithm. In addition, features may be extracted from the change in a diameter of the blood vessel and bio-information may be estimated using a bio-information estimation model.

The storage 620 may store information on one or more control criteria for controlling the ultrasonic device 710 and the pressurizing device 720. For example, the information may include information on an ultrasonic frequency, an ultrasonic transmission period, an ultrasound image acquisition time, a pressurization start time, a pressure release time, a pressurization intensity, and the like. In addition, the information may include information on a bio-information estimation model, an algorithm for calculating a diameter of a blood vessel by analyzing an ultrasound image, and the like. Also, information on personal characteristics of the user may be stored. Moreover, the storage 620 may store the ultrasound images received from the ultrasonic device 710 and the processing result of the processor 610.

The output interface 630 may output the ultrasound images received from the ultrasonic device 710 and the processing result of the processor 610. Referring to FIG. 7A, the output interface 630 may display a blood sugar estimation result in the display DP. Also, referring to FIG. 7B, the output interface 630 may divide the display DP into a first area DA1 and a second area DA2, and output a graph GR showing a change in a diameter of a blood vessel in the first area DA1 and a blood sugar estimation result and warning information regarding a risk of prediabetes and/or hyperglycemia in the second area DA2. These are merely examples and the blood sugar estimation result is not limited thereto.

Figure 8:
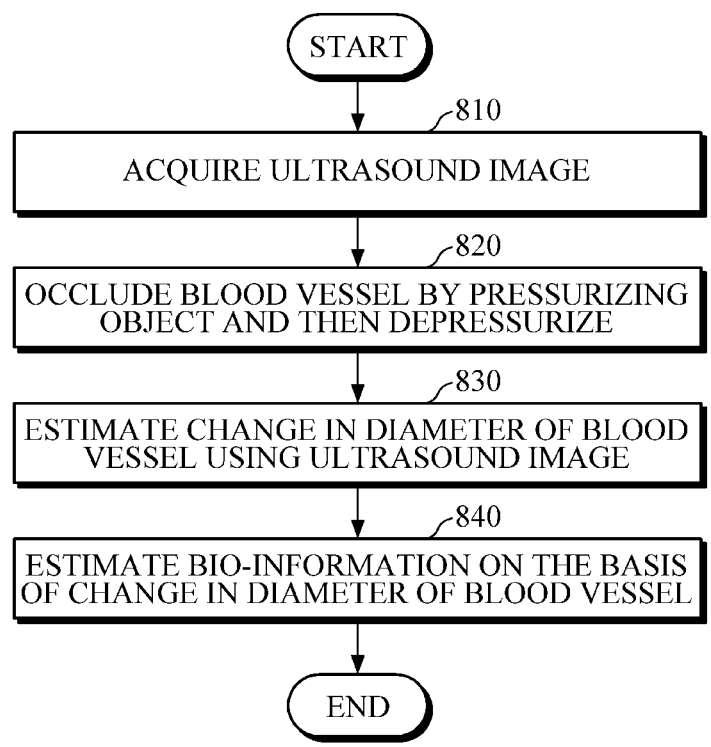
FIG. 8 is a flowchart illustrating a method of estimating bio-information according to an example embodiment.

FIG. 8 is a flowchart illustrating a method of estimating bio-information according to an example embodiment. The method shown in FIG. 8 is an example embodiment of a method that may be performed by any one of the apparatuses 100 and 200 of FIGS. 1 and 2 for estimating bio-information. The apparatuses 100 and 200 for bio-information estimation has been described in detail above, and thus a description thereof will be given briefly to avoid redundancy.

First, an ultrasound image may be acquired through an ultrasound image acquirer (810). The ultrasound image acquirer may transmit ultrasonic waves to an object and acquire the ultrasound image based on a reflected wave reflected from the object.

Then, when a predetermined period of time elapses after the start of the ultrasound image acquisition, pressure may be applied to the object through a pressurizer to occlude a blood vessel, and the pressure may be released after a predetermined period of time elapses (820).

Subsequently, the change in a diameter of a blood vessel may be estimated by analyzing the ultrasound image (830).

Then, bio-information may be estimated based on the change in a diameter of the blood vessel. For example, features, such as a vascular contraction rate, a vascular dilation rate, a restoration degree of blood vessels, vascular diameter change trend information, and the like may be acquired from a graph of a change in a diameter of a blood vessel, and the bio-information may be estimated by combining one or more of the acquired features.

The example embodiments may be implemented as computer readable codes in a computer readable record medium. The computer readable record medium includes all types of record media in which computer readable data read by a computer system are stored.

Examples of the computer readable record medium include a ROM, a RAM, a compact disc (CD)-ROM, a magnetic tape, a floppy disk, and an optical data storage. Further, the computer readable record medium may be implemented in a form of a carrier wave such as Internet transmission. In addition, the computer readable record medium may be distributed to computer systems over a network, in which computer readable codes may be stored and executed in a distributed manner. Further, functional programs, codes, and code segments for implementing the example embodiments may be easily inferred by a skilled computer programmer in the art.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing operations may employ any number of related art techniques for electronics configuration, signal processing and/or control, data processing and the like.

A number of example embodiments have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for estimating bio-information, the apparatus comprising:
   an ultrasound image acquirer configured to acquire ultrasound images of an object;
   a pressurizer configured to apply pressure to the object to occlude a blood vessel; and
   a processor configured to:
      estimate a change in a diameter of the blood vessel using the ultrasound images acquired by the ultrasound image acquirer before and after an occlusion of the blood vessel;
      estimate a first vascular dilation rate based on the change in the diameter of the blood vessel, which is estimated in a fasting state, and estimate a second vascular dilation rate based on the change in the diameter of the blood vessel, which is estimated in a state in which a blood sugar level is elevated; and
estimate an amount of a change in blood sugar by using the first vascular dilation rate and the second vascular dilation rate.

2. The apparatus of claim 1, wherein the ultrasound image acquirer is further configured to transmit ultrasonic waves to the object, receive a reflected wave reflected from the object, and generate the ultrasound images based on the received reflected wave.

3. The apparatus of claim 1, wherein the pressurizer comprises a cuff.

4. The apparatus of claim 1, wherein the processor is further configured to, based on a request for estimating the amount of the change in blood sugar, control the ultrasound image acquirer to acquire the ultrasound images, and control the pressurizer to apply the pressure to the object during a period of time, and release the pressure after an elapse of the period of time.

5. The apparatus of claim 1, wherein the processor is further configured to, based on the estimated change in the diameter of the blood vessel, acquire at least one feature among a vascular contraction rate, a restoration rate, and a vascular diameter change trend of the blood vessel, and estimate the amount of the change in blood sugar based on the acquired at least one feature along with the first vascular dilation rate and the second vascular dilation rate.

6. The apparatus of claim 5, wherein the processor is further configured to generate a graph representing the estimated change in the diameter of the blood vessel over a period of time and acquire the at least one feature based on the generated graph.

7. The apparatus of claim 5, wherein the processor is further configured to acquire the vascular contraction rate based on a difference between a diameter of the blood vessel before pressurization and a reduced blood vessel diameter after the pressurization.

8. The apparatus of claim 5, wherein the processor is further configured to acquire the first vascular dilation rate or the second vascular dilation rate based on a difference between a diameter of the blood vessel before pressurization and a diameter of a dilated blood vessel.

9. The apparatus of claim 5, wherein the processor is further configured to acquire the restoration rate of the blood vessel based on a slope between a diameter of a dilated blood vessel at a first time point at which the dilated blood vessel occurs upon releasing the pressure and a diameter of the blood vessel after a predetermined time from the first time point.

10. The apparatus of claim 5, wherein the processor is further configured to, based on the acquired at least one feature, estimate the amount of the change in blood sugar using a bio-information estimation model, the bio-information estimation model defining a correlation between the at least one feature and the amount of the change in blood sugar.

11. The apparatus of claim 1, further comprising an output interface configured to output at least one of the ultrasound images, the change in the diameter of the blood vessel, and a result of estimating the amount of the change in blood sugar.

12. A method of estimating bio-information, the method comprising:
acquiring, through an ultrasound image acquirer, ultrasound images of an object;
pressurizing, through a pressurizer, the object to occlude a blood vessel;
estimating, by a processor, a change in a diameter of the blood vessel using the ultrasound images acquired by the ultrasound image acquirer before and after an occlusion of the blood vessel;
estimating, by the processor, a first vascular dilation rate based on the change in the diameter of the blood vessel, which is estimated in a fasting state, and estimating, by the processor, a second vascular dilation rate based on the change in the diameter of the blood vessel, which is estimated in a state in which a blood sugar level is elevated; and
estimating, by the processor, an amount of a change in blood sugar by using the first vascular dilation rate and the second vascular dilation rate.

13. The method of claim 12, wherein the estimating the amount of the change in blood sugar comprises acquiring, based on the change in the diameter of the blood vessel, at least one feature among a vascular contraction rate, a restoration rate, and a vascular diameter change trend of the blood vessel, and estimating the amount of the change in blood sugar based on the acquired at least one feature along with the first vascular dilation rate and the second vascular dilation rate.

14. The method of claim 13, wherein the acquiring the at least one feature comprises acquiring the vascular contraction rate based on a difference between a diameter of the blood vessel before pressurization and a reduced blood vessel diameter after the pressurization.

15. The method of claim 13, wherein the acquiring the at least one feature comprises acquiring the first vascular dilation rate or the second vascular dilation rate based on a difference between a diameter of the blood vessel before pressurization and a diameter of a dilated blood vessel.

16. The method of claim 13, wherein the acquiring the at least one feature comprises acquiring the restoration rate of the blood vessel based on a slope between a diameter of a dilated blood vessel at a first time point at which the dilated blood vessel occurs upon releasing pressure and a diameter of the blood vessel after a predetermined time from the first time point.

17. The method of claim 13, wherein the estimating the amount of the change in blood sugar based on the acquired at least one feature comprises estimating the amount of the change in blood sugar using a bio-information estimation model, the bio-information estimation model defining a correlation between the at least one feature and the amount of the change in blood sugar.

18. The method of claim 12, further comprising outputting at least one of the change in the diameter of the blood vessel, and a result of estimating the amount of the change in blood sugar.

19. An ultrasonic device comprising:
an ultrasound image acquirer configured to transmit ultrasonic waves to an object and acquire ultrasound images based on a reflected wave reflected from the object; and
a processor configured to:
control a pressurizing device to occlude a blood vessel of the object;
estimate a change in a diameter of the blood vessel based on the ultrasound images acquired by the ultrasound image acquirer before and after an occlusion of the blood vessel;
estimate a first vascular dilation rate based on the change in the diameter of the blood vessel, which is estimated in a fasting state, and estimate a second vascular dilation rate based on the change in the diameter of the blood vessel, which is estimated in a state in which a blood sugar level is elevated; and estimate an amount of a change in blood sugar by using the first vascular dilation rate and the second vascular dilation rate.

20. The ultrasonic device of claim 19, further comprising a communication interface configured to transmit a control signal generated by the processor to the pressurizing device.

21. The ultrasonic device of claim 20, wherein the communication interface is further configured to transmit at least one of the ultrasound images, the change in the diameter of the blood vessel, and a result of estimating the amount of the change in blood sugar to a mobile device.

22. The ultrasonic device of claim 19, wherein the processor is further configured to acquire, based on the change in the diameter of the blood vessel, at least one feature among a vascular contraction rate, a restoration rate, and a vascular diameter change trend of the blood vessel, and estimate the amount of the change in blood sugar using the acquired at least one feature along with the first vascular dilation rate and the second vascular dilation rate.

23. The ultrasonic device of claim 19, further comprising an output interface configured to output at least one of the ultrasound images, the change in the diameter of the blood vessel, and a result of estimating the amount of the change in blood sugar.

24. The ultrasonic device of claim 19, further comprising:
a main body in which the ultrasound image acquirer and the processor are mounted; and
a strap configured to be connected to the main body.

25. A mobile device comprising:
a communication interface configured to transmit a first control signal to an ultrasonic device and a second control signal to a pressurizing device and receive ultrasound images of an object from the ultrasonic device; and
a processor configured to:
generate the first control signal and the second control signal;
estimate a change in a diameter of a blood vessel based on the ultrasound images transmitted from the ultrasonic device before and after an occlusion of the blood vessel;
estimate a first vascular dilation rate based on the change in the diameter of the blood vessel, which is estimated in a fasting state, and estimate a second vascular dilation rate based on the change in the diameter of the blood vessel, which is estimated in a state in which a blood sugar level is elevated; and
estimate an amount of a change in blood sugar by using the first vascular dilation rate and the second vascular dilation rate.

26. The mobile device of claim 25, wherein the processor is further configured to:
generate, based on a request for estimating the amount of the change in blood sugar, the first control signal for controlling the ultrasonic device to acquire the ultrasound images;
generate the second control signal for controlling the pressurizing device to pressurize the object during a period of time; and
generate a third control signal for controlling the pressurizing device to release pressure after an elapse of the period of time.

27. The mobile device of claim 25, wherein the processor is further configured to, based on the estimated change in the diameter of the blood vessel, acquire at least one feature among a vascular contraction rate, a restoration rate, and a vascular diameter change trend of the blood vessel, and estimate the amount of the change in blood sugar based on the acquired at least one feature along with the first vascular dilation rate and the second vascular dilation rate.

28. The mobile device of claim 25, further comprising an output interface configured to output at least one of the ultrasound images, the change in the diameter of the blood vessel, and a result of estimating the amount of the change in blood sugar.

* * * * *